US008779190B2

(12) United States Patent
Tani et al.

(10) Patent No.: US 8,779,190 B2
(45) Date of Patent: Jul. 15, 2014

(54) PROCESS FOR PRODUCING SULFUR-CONTAINING AMINO ACID OR SALT THEREOF

(75) Inventors: Kazuyasu Tani, Kobe (JP); Taro Hirose, Suita (JP); Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/636,238

(22) PCT Filed: Mar. 24, 2011

(86) PCT No.: PCT/JP2011/058157

§ 371 (c)(1), (2), (4) Date: Sep. 20, 2012

(87) PCT Pub. No.: WO2011/118849

PCT Pub. Date: Sep. 29, 2011

(65) Prior Publication Data

US 2013/0012737 A1 Jan. 10, 2013

(30) Foreign Application Priority Data

Mar. 25, 2010 (JP) ................................ 2010-069478
Oct. 26, 2010 (JP) ................................ 2010-239425

(51) Int. Cl.
*C07C 319/20* (2006.01)

(52) U.S. Cl.
USPC .......................................................... 562/559

(58) Field of Classification Search
CPC ..................................................... C07C 323/58
See application file for complete search history.

(56) References Cited

U.S. PATENT DOCUMENTS 4,073,804 A * 2/1978 Hearon et al. ................ 562/575
4,400,533 A * 8/1983 aus der Funten et al. ..... 562/443
5,416,019 A * 5/1995 Leuchtenberger et al. 435/252.1
5,770,769 A 6/1998 Geiger et al.
6,884,887 B1 4/2005 Riermeier et al.
2008/0009649 A1 1/2008 Hateley et al.

FOREIGN PATENT DOCUMENTS

JP 61-91159 A 5/1986
JP 9-176111 A 7/1997
JP 2008-501738 A 1/2008
WO 2006/113085 A2 10/2006

OTHER PUBLICATIONS

White et al, Basic Energy Sciences Advisory Committee Subpanel Workshop Report, Opportunities for Catalysis in the 21st Century, 2002, pp. 1-47.*

Chan et al, Applied Catalysis, A: General, Catalytic reductive amination of alpha- Ketocarboxylic Acids as a Useful Route to Amino Acids ,1994, 119(1), pp. L1-L5.*

First Office Action issued Jul. 2, 2013 in counterpart Chinese Patent Application No. 201180015242.2 to Sumitomo Chemical Co., Ltd., with translation.

Andrey Galkin, et al., "Synthesis of Optically Active Amino Acids from α-Keto Acids with *Escherichia coli* Cells Expressing Heterologous Genes", Applied and Environmental Microbiology, Dec. 1997, vol. 63, No. 12, pp. 4651-4656.

"Industrial Organic Chemistry", Tokyo Kagaku-Dojin 1978, pp. 273-275, Partial English Translation.

Franz Effenberger et al., "Synthesen von DL-Cysteinen ausghend von Acrylsaure-Derivaten", Chem. Ber., 1988, pp. 2209-2223, vol. 121.

Translation of International Preliminary Report on Patentability mailed Oct. 4, 2012 in International Application No. PCT/JP2011/058157 to Sumitomo Chemical Co., Ltd.

Supplementary European Search Report issued in corresponding EP Application No. 11759649.4, dated Dec. 17, 2013.

Vedha-Peters K. et al., "Creation of a broad-range and highly stereoselective D-amino acid dehydrogenase for the one-step synthesis of D-amino acids", Journal of the American Chemical Society, ACS Publications, vol. 128, No. 33, Aug. 23, 2006, pp. 10923-10929.

Baldwin J. E. et al., "Application of *E. Coli* Aspartate Transaminase to Amino Acid Synthesis", Tetrahedron Letters, vol. 28, No. 32, Jan. 1, 1987, pp. 3745-3746.

Asano Y. et al., "Enantioselective Synthesis of (S)-Amino Acids by Phenylalanine Dehydrogenase from *Bacillus Sphaericus*: Use of Natural and Recombinant Enzymes", The Journal of Organic Chemistry, American Chemical Society, vol. 55, No. 21, Jan. 1, 1990, pp. 5567-5571.

Chinese Office Action issued in corresponding CN Application No. 201180015242.2, dated Feb. 26, 2014.

* cited by examiner

*Primary Examiner* — Paul A Zucker
(74) *Attorney, Agent, or Firm* — Sughrue Mion, PLLC

(57) ABSTRACT

According to the present invention, a new process for producing a sulfur-containing amino acid without using of hydrogen cyanide or sodium azide which requires careful handling as a raw material can be provided. The present invention relates to a process for producing a sulfur-containing amino acid represented by the following formula (1) or a salt thereof:

$$R^1—S—(CH_2)_n—\underset{NH_2}{\overset{H}{C}}—CO_2H \quad (1)$$

wherein $R^1$ is an alkyl group having 1 to 12 carbon atoms and optionally having substituents or a cycloalkyl group having 3 to 12 carbon atoms and optionally having substituents, and n is an integral number of from 1 to 4, comprising a step of reacting a sulfur-containing 2-keto-carboxylic acid represented by the formula (2) or a salt thereof:

$$R^1—S—(CH_2)_n—\underset{\| \atop O}{C}—CO_2H \quad (2)$$

wherein $R^1$ and n mean the same as defined above, with ammonia and hydrogen in the presence of a transition metal catalyst.

4 Claims, No Drawings

PROCESS FOR PRODUCING SULFUR-CONTAINING AMINO ACID OR SALT THEREOF

TECHNICAL FIELD

The present application is filed, claiming the priorities based on the Japanese Patent Application Nos. 2010-069478 (filed on Mar. 25, 2010) and 2010-239425 (filed on Oct. 26, 2010), and a whole of the contents of these applications is incorporated herein by reference.

The present invention relates to a process for producing a sulfur-containing amino acid and a salt thereof.

BACKGROUND ART

Sulfur-containing amino acids such as methionine and S-alkyl cysteine exist commonly in the all organisms, and they are useful components for many important biological reactions. Particularly, methionine is an essential amino acid, which is an important compound for use as a feed additive.

For example, the following method is disclosed in "industrial organic chemistry", Tokyo Kagaku-Dojin, 1978, pp. 273-275: 3-(methylthio)propanal obtained by addition of methanethiol to acrolein is reacted with hydrogen cyanide to obtain 2-hydroxyl-4-methylthiobutyronitrile; and then, the 2-hydroxyl-4-methylthiobutyronitrile is reacted with ammonium carbonate to obtain a substituted hydantoin and thereafter, the substituted hydantoin is hydrolyzed by an alkali. In addition, the following method is disclosed in "Chem. Ber.", vol. 121, 1988, pp. 2209-2223: methanethiol is added to methyl 2-chloroacrylate; and then, the resultant adduct is reacted with a sodium azide and thereafter, the resultant product is hydrogenated under acidic conditions.

DISCLOSURE OF INVENTION

Problem to be Solved by the Invention

However, the methods disclosed in the above documents involve use of hydrogen cyanide or sodium azide as a raw material. These compounds require careful handling.

Under such a circumstance, there has been demanded a new process for producing sulfur-containing amino acids without requiring use of hydrogen cyanide or sodium azide etc. as a raw material.

Means for Solving the Problem

As a result of the present inventors' intensive studies for solving the above-described problem, the present invention is accomplished.

The present invention provides the followings:

[1] A process for producing a sulfur-containing amino acid represented by the following formula (1) or a salt thereof:

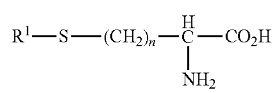

(1)

wherein $R^1$ is an alkyl group having 1 to 12 carbon atoms and optionally having substituents or a cycloalkyl group having 3 to 12 carbon atoms and optionally having substituents, and n is an integral number of from 1 to 4, comprising a step of reacting a sulfur-containing 2-ketocarboxylic acid represented by the formula (2) or a salt thereof:

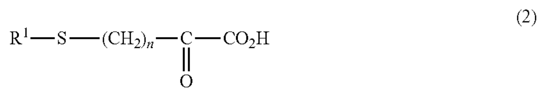

(2)

wherein $R^1$ and n mean the same as defined above, with ammonia and hydrogen in the presence of a transition metal catalyst.

[2] The process defined in the above item [1], wherein, in the step, the sulfur-containing 2-ketocarboxylic acid represented by the formula (2) or the salt thereof is reacted with ammonia and hydrogen in the presence of a solvent in addition to the transition metal catalyst.

[3] The process defined in the above item [2], wherein the solvent is methanol or water.

[4] The process defined in the above items [1] to [3], wherein the transition metal catalyst is a catalyst in which one or more transition metals selected from the group consisting of ruthenium, rhodium, palladium, platinum and iridium are supported on a support.

[5] The process defined in the above item [4], wherein the support is one or more supports selected from the group consisting of an activated carbon, alumina, silica and zeolite.

[6] The process defined in the above items [1] to [3], wherein the transition metal catalyst is one or more catalysts selected from the group consisting of a sponge nickel, a sponge cobalt, a sponge copper and a noble metal catalyst.

[7] The process defined in the above items [1] to [6], wherein, in the step, the sulfur-containing 2-ketocarboxylic acid represented by the formula (2) or a salt thereof is reacted with ammonia and hydrogen at a temperature of from 0 to 100° C.

According to the present invention, a new process for producing a sulfur-containing amino acid without requiring use of hydrogen cyanide or sodium azide as a raw material can be provided.

MODES FOR CARRYING OUT THE INVENTION

Hereinafter, the present invention will be described in detail.

A salt of the sulfur-containing 2-ketocarboxylic acid represented by the formula (2) means a salt in which a hydrogen ion dissociable from the carboxyl group is substituted by a cation. Examples of the cation include alkali metal ions such as a lithium ion, a sodium ion, and a potassium ion; alkaline-earth metal ions such as a calcium ion, and a magnesium ion; quaternary ammonium ions such as a tetramethylammonium ion, and a tetrabutylammonium ion; and an ammonium ion.

Hereinafter, the sulfur-containing 2-ketocarboxylic acid represented by the formula (2) and the salt thereof are sometimes collectively referred to as the compound (2).

A salt of the sulfur-containing amino acid represented by the formula (1) means a salt of the sulfur-containing amino acid of the formula (1) with an acid such as hydrochloric acid, benzoic acid and tartaric acid, or a salt in which a hydrogen ion dissociable from the carboxyl group is substituted by a cation. Examples of the cation include alkali metal ions such as a lithium ion, a sodium ion, and a potassium ion; alkaline-earth metal ions such as a calcium ion, and a magnesium ion; quaternary ammonium ions such as a tetramethylammonium ion, and a tetrabutylammonium ion; and an ammonium ion.

Hereinafter, the sulfur-containing amino acid represented by the formula (1) and the salt thereof are sometimes collectively referred to as the compound (1).

In the compounds of the above-described formula (1) or (2), $R^1$ is an alkyl group having 1 to 12 carbon atoms and optionally having substituents or a cycloalkyl group having 3 to 12 carbon atoms and optionally having substituents, and n is an integral number of from 1 to 4.

Examples of the alkyl group having 1 to 12 carbon atoms include a methyl group, an ethyl group, a propyl group, an isopropyl group, a butyl group, an isobutyl group, a sec-butyl group, a tert-butyl group, a pentyl group, an octyl group and a decyl group. Examples of the cycloalkyl group having 3 to 12 carbon atoms include a cyclopropyl group, a cyclobutyl group, a cyclopentyl group and a cyclohexyl group.

As the substituents which may be included in the alkyl group having 1 to 12 carbon atoms and the cycloalkyl group having 3 to 12 carbon atoms, there are mentioned aryl groups having 6 to 20 carbon atoms such as a phenyl group, a 1-naphthyl group, a 2-naphthyl group and a 4-methylphenyl group; alkoxy groups having 1 to 12 carbon atoms such as a methoxy group, an ethoxy group, a propoxy group, an isopropoxy group, a butoxy group, an isobutoxy group, a sec-butoxy group and a tert-butoxy group; aryloxy groups having 6 to 20 carbon atoms such as a phenoxy group, a 2-methylphenoxy group and a 4-methylphenoxy group; perfluoroalkyloxy groups having 1 to 6 carbon atoms such as a trifluoromethoxy group and a pentafluoromethoxy group; and at least one group selected from the group consisting of halogen atoms such as a fluorine atom and a chlorine atom.

The aryl group having 6 to 20 carbon atoms, the alkoxy group having 1 to 12 carbon atoms and the aryloxy group having 6 to 20 carbon atoms may additionally have a group selected from the group consisting of an aryl group having 6 to 20 carbon atoms, an alkoxy group having 1 to 12 carbon atoms and an aryloxy group having 6 to 20 carbon atoms.

As to $R^1$, specific examples of the alkyl group having to 12 carbon atoms and having substituents and the cycloalkyl group having 3 to 12 carbon atoms and having substituents include a benzyl group, a naphthalene-1-ylmethyl group, a naphthalene-2-ylmethyl group, a 4-methylbenzyl group, a 3,4-dimethylbenzyl group, a 4-methoxybenzyl group, a 3,4-dimethoxybenzyl group, a 4-phenylbenzyl group, a 4-phenoxybenzyl group, a methoxymethyl group, an ethoxymethyl group, an isopropyloxymethyl group, a butyloxymethyl group, an isobutyloxymethyl group, a sec-butyloxymethyl group, a tert-butyloxymethyl group, a phenoxymethyl group, a 2-methylphenoxymethyl group, a 4-methylphenoxymethyl group, a 1-phenylethyl group, a 2-phenylethyl group, a 1-(naphthalene-1-yl)ethyl group, a 1-(naphthalene-2-yl) ethyl group, a 1-(4-methylphenyl)ethyl group, a 1-(3,4-dimethylphenyl)ethyl group, a 1-(4-methoxyphenyl)ethyl group, a 1-(3,4-dimethoxyphenyl)ethyl group, a 1-(4-phenylphenyl) ethyl group, a 1-(4-phenoxyphenyl)ethyl group, a 2-(methoxy)ethyl group, a 2-(ethoxy)ethyl group, a 2-(isopropyloxy) ethyl group, a 2-(butyloxy)ethyl group, a 2-(isobutyloxy) ethyl group, a 2-(sec-butyloxy)ethyl group, a 2-(tert-butyloxy)ethyl group, a 2-(phenoxy)ethyl group, a 2-(2-methylphenoxy)ethyl group, a 2-(4-methylphenoxy)ethyl group, a 2-phenylcyclopropyl group and a 4-phenylcyclohexyl group.

$R^1$ is preferably an alkyl group having 1 to 12 carbon atoms and optionally having a substituent, and more preferably a methyl group, an ethyl group, a propyl group, an isopropyl group, a butyl group, a tert-butyl group or a benzyl group, and particularly preferably a methyl group.

Specific examples of the compound (2) include 3-methylthio-2-oxopropionic acid, 3-tert-butylthio-2-oxopropionic acid, 3-benzylthio-2-oxopropionic acid, 3-ethylthio-2-oxopropionic acid, 4-methylthio-2-oxobutanoic acid, 4-ethylthio-2-oxobutanoic acid, 2-oxo-4-(propylthio)butanoic acid, 4-benzylthio-2-oxobutanoic acid, 5-methylthio-2-oxopentanoic acid, 5-(ethylthio)-2-oxopentanoic acid, 2-oxo-5-(propylthio)pentanoic acid, 5-(benzylthio)-2-oxopentanoic acid, 6-methylthio-2-oxohexanoic acid, 6-(ethylthio)-2-oxohexanoic acid, 2-oxo-6-(propylthio)hexanoic acid, 6-(benzylthio)-2-oxohexanoic acid and the salts thereof.

As the compound (2), a commercially available product may be used, and also they can be synthesized according to, for example, the method described in Bull. Agr. Chem. Soc. Japan, vol. 21, No. 6, pp. 333-336, 1957, or Journal of Labelled Compounds and Radiopharmaceuticals, vol. XXXVI, No. 5, pp. 431-437, 1995.

Specific examples of the compound (1) include 2-amino-3-(methylthio)propionic acid, 2-amino-3-(tert-butylthio)propionic acid, 2-amino-3-(benzylthio)propionic acid, 2-amino-3-(ethylthio)propionic acid, 2-amino-4-(methylthio) butanoic acid (i.e. methionine), 2-amino-4-(ethylthio) butanoic acid, 2-amino-4-(propylthio)butanoic acid, 2-amino-4-(benzylthio)butanoic acid, 2-amino-5-(methylthio)pentanoic acid, 2-amino-5-(ethylthio)pentanoic acid, 2-amino-5-(propylthio)pentanoic acid, 2-amino-5-(benzylthio)pentanoic acid, 2-amino-6-(methylthio)hexanoic acid, 2-amino-6-(ethylthio)hexanoic acid, 2-amino-6-(propylthio)hexanoic acid, 2-amino-6-(benzylthio)hexanoic acid and the salts thereof.

The process of the present invention comprises a step in which the compound (2) is reacted with ammonia and hydrogen in the presence of a transition metal catalyst. In this step, the compound (2) is converted to the compound (1).

Examples of the transition metal catalyst include nickel catalysts such as a reduced nickel catalyst, and a sponge nickel (Raney® nickel, etc.); cobalt catalysts such as a reduced cobalt catalyst, and a sponge cobalt (Raney® cobalt, etc.); copper catalysts such as a sponge copper (Raney® copper, etc.); and a noble metal catalyst such as ruthenium, rhodium, palladium, platinum and iridium. The reduced metal catalysts such as the reduced nickel catalyst, the reduced cobalt catalyst and the reduced copper catalyst are catalysts obtained by reducing a metal oxide or hydroxide itself or obtained by reducing a metal oxide or hydroxide supported on a support. The transition metal catalyst is preferably one or more catalysts selected from the group consisting of a sponge nickel, a sponge cobalt, a sponge copper and a noble metal catalyst.

The noble metal catalyst, specifically a transition metal selected from the group consisting of ruthenium, rhodium, palladium, platinum and iridium, is preferably supported on a support. As the support, for example, at least one support selected from the group consisting of an activated carbon, alumina, silica and zeolite is preferable. Of these, a palladium supported on an activated carbon or a rhodium supported on the activated carbon is preferable.

As the transition metal catalyst, a commercially available product may be used, and also, it can be prepared by using any known method. The transition metal catalyst is used such that a transition metal atom is contained in an amount preferably from 0.001 to 2 parts by weight, more preferably from 0.0001 to 0.2 parts by weight, per part by weight of the compound (2).

The ammonia can be used in either form of liquid ammonia, an ammonia gas or an ammonia solution. Preferably, an ammonia solution is used, and more preferably an ammonia water or an ammonia/methanol solution is used. If the ammonia water is used, the concentration is preferably from 10 to 35% by weight. Also, ammonia may form a salt with an inorganic acid such as hydrochloric acid and sulfuric acid, or with a carboxylic acid such as formic acid and acetic acid.

The amount of the ammonia to be used is preferably 1 mol or more per 1 mol of the compound (2). The upper limit is not limited, but it is usually 500 mol per 1 mol of the compound (2).

As the hydrogen, a commercial hydrogen gas may be used, and also, the hydrogen prepared from, for example, formic acid or acetic acid by any known method can be used. If the hydrogen gas is used, the partial pressure is preferably less than or equal to 10 MPa, and more preferably from 0.01 to 5 MPa, and especially preferably from 0.02 to 2 MPa, and particularly preferably 0.05 to 0.8 MPa.

The reaction of the compound (2) with ammonia and hydrogen is preferably carried out in the presence of a solvent. The solvent is preferably inactive to the reaction. Examples of the solvent include aliphatic hydrocarbon solvents such as pentane, hexane, isohexane, heptane, isoheptane, octane, isooctane, nonane, isononane, decane, isodecane, undecane, dodecane, cyclopentane, cyclohexane, methylcyclohexane, tert-butylcyclohexane and petroleum ether; ester solvents such as tetrahydrofuran, methyltetrahydrofuran, diethyl ether, dipropyl ether, diisopropyl ether, dibutyl ether, dipentyl ether, dihexyl ether, diheptyl ether, dioctyl ether, tert-butyl methyl ether, cyclopentyl methyl ether, 1,2-dimethoxyethane, diethylene glycol dimethyl ether; alcohol solvents such as methanol, ethanol, 1-propanol, 2-propanol, 1-butanol, isobutanol, tert-butyl alcohol, 1-pentanol, 2-pentanol, isopentanol, 1-hexanol, 2-hexanol, isohexanol, 1-heptanol, 2-heptanol, 3-heptanol, isoheptanol, ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol mono-tert-butyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol mono-tert-butyl ether; ester solvents such as ethyl acetate, propyl acetate, isopropyl acetate, butyl acetate, isobutyl acetate, tert-butyl acetate, amyl acetate, isoamyl acetate; aprotic polar solvents such as dimethylsulfoxide, sulfolane, N,N-dimethylformamide, N,N-dimethylacetamide, N,N-dimethylpropionamide, N-methylpyrrolidone, γ-butyrolactone, dimethyl carbonate, diethyl carbonate, ethylene carbonate, propylene carbonate, 1,3-dimethyl-2-imidazoline, 1,3-dimethyl-3,4,5,6-tetrahydro-2(1H)-pyridinone; water; and the mixture thereof. Among them, the alcohol solvents or water is preferable, and methanol or water is more preferable.

The amount of the solvent to be used is preferably from 1 to 200 ml, more preferably from 10 to 150 ml, per 1 g of the compound (2).

The order of blending of each reactant is not particularly limited. A method for blending each reactant includes a method comprising mixing the compound (2) with ammonia and a transition metal catalyst, and then adding hydrogen to the resultant mixture; or a method comprising mixing the compound (2) with ammonium formate, and optionally adjusting to any desired pH by adding formic acid, followed by adding a transition metal catalyst to the resultant mixture.

The reaction temperature is preferably from 0 to 100° C., more preferably from 20 to 90° C. The reaction time may vary depending on the reaction temperature, the reactants to be used, the amount of the solvent added and the hydrogen partial pressure etc. The reaction time is usually from 1 to 24 hours. The degree of the reaction progress can be confirmed by means of thin-layer chromatography, gas chromatography, high-performance liquid chromatography or the like.

After completion of the reaction, the compound (1) can be obtained by subjecting the resultant reaction mixture to a post-treatment such as filtration, neutralization, extraction and washing with water, and then subjecting to an isolation treatment such as distillation and crystallization. The post-treatment and the isolation treatment may be carried out optionally after controlling the temperature of the reaction mixture. Specifically, in this case, after controlling the temperature of the reaction mixture to be at around room temperature, or without controlling the temperature, the resultant reaction mixture filtrates to remove the transition metal catalyst therefrom, followed by neutralizing the resultant filtrate to precipitate the compound (1). And then, the precipitated compound (1) can be recovered finally by filtration. If the resultant reaction mixture is basic, the neutralization is carried out by mixing the reaction mixture with an acid such as a hydrochloric acid or a carbonic acid. If the resultant reaction mixture is acidic, the neutralization is carried out by mixing the reaction mixture with a base such as a sodium carbonate, a sodium bicarbonate or a potassium carbonate. The transition metal removed by the filtration and the compound (1) recovered by the filtration may be washed with the above-mentioned solvent. In addition, the recovered compound (1) may be dried under reduced pressure. If the reaction mixture contains ammonia, the ammonia can be removed from the mixture, for example, by blowing hydrogen gas through the mixture.

The isolated compound (1) may be purified by recrystallization; extractive purification; distillation; adsorption treatment to activated carbon, silica, alumina or the like; purification treatment, for example, chromatography method such as silica gel column chromatography.

EXAMPLES

The present invention will be described in more detail by way of the Examples.

In the Examples 1 to 11, the reaction mixture was analyzed by high-performance liquid chromatography (manufactured by Shimadzu Corporation) under the following condition. In addition, the conversion and selectivity were calculated based on the following formulas. In the Example 12, the content of 2-amino-4-(methylthio)butanoic acid was determined by a high-performance liquid chromatography internal standard method. As an internal standard substrate, the 2-amino-4-(methylthio) butanoic acid prepared separately was used.

Conditions for analysis:

LC column: Lichrosorb-RP-8
Column temperature: 40° C.
Mobile phase: acetonitrile/water: 5/95
additive: Sodium 1-Pentanesulfonate
concentration of additive: 2.5 mmol/L
pH of mobile phase: pH 3
(adjustment by adding 40% phosphoric acid)
Flow rate: 1.5 ml/min.
Detection wavelength: 210 nm
Measurement time: 60 min.

Calculation of conversion:

Conversion (%)=100(%)−[peak area (%) of the compound (2)]

Calculation of selectivity:

Selectivity (%)=[peak area (%) of the compound (1)]/[peak area (%) of all products]×100

Example 1

To a 60 ml autoclave were added a sodium 4-(methylthio)-2-oxobutylate (50 mg), 7 mol/L ammonia/methanol solution (12.6 ml) and 5% by weight Pd/C (product of Wako Pure Chemical Industries, Ltd.) (32 mg), and the resulting mixture was stirred. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 99% or more, and the selectivity of 2-amino-4-(methylthio)butanoic acid was 90%.

Reference Example 1

To a 60 ml autoclave are added a sodium 4-(methylthio)-2-oxobutylate (50 mg), 7 mol/L ammonia/methanol solution (12.6 ml) and 5% by weight Pd/C (product of Wako Pure Chemical Industries, Ltd.) (32 mg), and the resulting mixture is stirred. Hydrogen is added to the autoclave under pressure to give a gauge pressure of 0.5 MPaG, and then, the temperature is elevated to 50° C. and stirred for 6 hours. After the resulting reaction mixture is cooled to room temperature, the internal pressure of the autoclave is released to normal pressure, and then, ammonia not consumed in the reaction is removed from the reaction mixture by introducing nitrogen gas to the reaction mixture. Then, the reaction mixture is neutralized by blowing carbon dioxide into the mixture. Optionally water is added to the mixture, and the filtrate obtained by filtration of the mixture is concentrated to isolate the 2-amino-4-(methylthio)butanoic acid.

Example 2

To a 60 ml autoclave were added a sodium 4-(methylthio)-2-oxobutylate (50 mg), 7 mol/L ammonia/methanol solution (12.6 ml) and 5% by weight Pd/C (product of Wako Pure Chemical Industries, Ltd.)(32 mg), and the resulting mixture was stirred. Under a hydrogen atmosphere (normal pressure), the resulting mixture was stirred for 6 hours at 50° C. Then, a part of the resulting reaction mixture was analyzed by high-performance liquid chromatography. As a result, the conversion of sodium 4-(methylthio)-2-oxobutylate was 99% or more, and the selectivity of 2-amino-4-(methylthio)butanoic acid was 83%.

Example 3

To a 60 ml autoclave were added a sodium 4-(methylthio)-2-oxobutylate (50 mg), 28% by weight ammonia water (5.4 g) and 5% by weight Pd/C (product of Wako Pure Chemical Industries, Ltd.) (32 mg), and the resulting mixture was stirred. Hydrogen was added to the autoclave under pressure to give a gauge pressure of 1.0 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 99% or more, and the selectivity of 2-amino-4-(methylthio)butanoic acid was 34%.

Example 4

To a 60 ml autoclave were added a sodium 4-(methylthio)-2-oxobutylate (44 mg), 28% by weight ammonia water (5.4 g) and 5% by weight Pd/C (product of Wako Pure Chemical Industries, Ltd.) (32 mg), and the resulting mixture was stirred. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 99% or more, and the selectivity of 2-amino-4-(methylthio)butanoic acid was 70%.

Example 5

To a 10 ml flask were added a sodium 4-(methylthio)-2-oxobutylate (50 mg), ammonium formate (370 mg) and water (5.0 g), and the pH of the resulting mixture was adjusted to pH 5.0 by adding formic acid to the mixture. After 5% by weight Pd/C (product of Wako Pure Chemical Industries, Ltd.) (60.5 mg) was added to the mixture, the temperature was elevated to 80° C., followed by stirring the mixture at the same temperature for 15 hours. Then, a part of the resulting reaction mixture was analyzed by high-performance liquid chromatography. As a result, the conversion of sodium 4-(methylthio)-2-oxobutylate was 84%, and the selectivity of 2-amino-4-(methylthio)butanoic acid was 42%.

Example 6

To a 50 ml autoclave were added a sodium 4-(methylthio)-2-oxobutylate (51 mg) and 28% by weight ammonia water (5.4 g), and the resulting mixture was stirred. Then, Raney® nickel (product of Degussa Co., Ltd.) (51 mg: wet weight) was added to the resulting mixture. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 94%, and the selectivity of 2-amino-4-(methylthio)butanoic acid was 10%.

Example 7

To a 50 ml autoclave were added a sodium 4-(methylthio)-2-oxobutylate (51 mg) and 28% by weight ammonia water (5.4 g), and the resulting mixture was stirred. Then, Raney® cobalt (product of Aldrich Co.) (51 mg: wet weight) was added to the resulting mixture. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 96%, and the selectivity of 2-amino-4-(methylthio)butanoic acid was 27%.

Example 8

To a 50 ml autoclave were added a sodium 4-(methylthio)-2-oxobutylate (51 mg) and 28% by weight ammonia water (5.4 g), and the resulting mixture was stirred. Then, Raney® copper (product of Strem Chemical Inc.) (51 mg: wet weight) was added to the resulting mixture. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 93%, and the selectivity of 2-amino-4-(methylthio)butanoic acid was 9.5%.

Example 9

To a 60 ml autoclave were added a sodium 4-(methylthio)-2-oxobutylate (50 mg), 7 mol/L ammonia/methanol solution (12.6 ml), and the resulting mixture was stirred. Then, Raney® nickel (product of Degussa Co., Ltd.) (51 mg: wet weight) was added to the resulting mixture. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 95%, and the selectivity of 2-amino-4-(methylthio)butanoic acid was 50%.

Example 10

To a 60 ml autoclave were added a sodium 4-(methylthio)-2-oxobutylate (50 mg), 7 mol/L ammonia/methanol solution (12.6 ml), and the resulting mixture was stirred. Then, Raney® cobalt (product of Aldrich Co.) (51 mg: wet weight) was added to the resulting mixture. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 91%, and the selectivity of 2-amino-4-(methylthio)butanoic acid was 52%.

Example 11

To a 60 ml autoclave were added a sodium 4-(methylthio)-2-oxobutylate (50 mg), 7 mol/L ammonia/methanol solution (12.6 ml), and the resulting mixture was stirred. Then, Raney® copper (product of Strem Chemical Inc.) (51 mg: wet weight) was added to the resulting mixture. Hydrogen was added to the autoclave under pressure to give a gauge pressure of 0.5 MPaG, and then, the temperature was elevated to 50° C. and stirred for 6 hours. Then, a part of the resulting reaction mixture was analyzed by high-performance liquid chromatography. As a result, the conversion of sodium 4-(methylthio)-2-oxobutylate was 82%, and the selectivity of 2-amino-4-(methylthio)butanoic acid was 13%.

Example 12

To a 60 ml autoclave were added a potassium 4-(methylthio)-2-oxobutylate aqueous solution (2.116 g, content: 14.5%), 28% by weight ammonia water (1.58 g) and 5% by weight Pd/C (product of Wako Pure Chemical Industries, Ltd.) (95 mg), and the resulting mixture was stirred. Hydrogen was added to the autoclave under pressure to give a gauge pressure of 0.5 MPaG, and then, the temperature was elevated to 40° C. and stirred for 13 hours. After the reaction mixture was cooled to room temperature, the mixture was filtered and the residue was washed with water. When $CO_2$ gas was introduced into the resulting solution (7.921 g, yield of DL-methionine: 72.9%) for 30 minutes, a solid deposition was confirmed. After the resulting solid was filtered, the residue was washed with water (0.5 g) and dried under vacuum to obtain 0.121 g of DL-methionine (content: 96%, yield: 68%). The analysis was carried out by an internal standard method, and the content and yield were calculated.

INDUSTRIAL APPLICABILITY

The present invention is useful as a process for producing the sulfur-containing amino acids such as methionine and the salts thereof.

The invention claimed is:

1. A process for producing a sulfur-containing amino acid represented by the following formula (1) or a salt thereof:

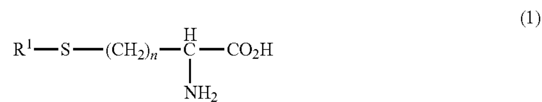

(1)

wherein $R^1$ is an alkyl group having 1 to 12 carbon atoms and optionally having substituents or a cycloalkyl group having 3 to 12 carbon atoms and optionally having substituents, and n is an integral number of from 1 to 4, comprising a step of reacting a salt of a sulfur-containing 2-ketocarboxylic acid represented by the formula (2):

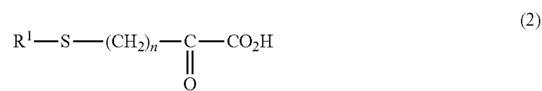

(2)

wherein $R^1$ and n mean the same as defined above, with ammonia and hydrogen in the presence of a transition metal catalyst, wherein the transition metal catalyst is selected from the group consisting of palladium supported on an activated carbon, rhodium supported on an activated carbon, sponge nickel, sponge cobalt and sponge copper catalysts.

2. The process according to claim 1, wherein, in the step, the salt of a sulfur-containing 2-ketocarboxylic acid represented by the formula (2) is reacted with ammonia and hydrogen in the presence of a solvent in addition to the transition metal catalyst.

3. The process according to claim 2, wherein the solvent is methanol or water.

4. The process according to claim 1, wherein, in the step, the salt of a sulfur-containing 2-ketocarboxylic acid represented by the formula (2) is reacted with ammonia and hydrogen at a temperature of from 0 to 100° C.

* * * * *